US00PP12248P2

(12) United States Plant Patent
Bergman

(10) Patent No.: US PP12,248 P2
(45) Date of Patent: Dec. 4, 2001

(54) CHRYSANTHEMUM PLANT NAMED 'AMBER POMONA'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/525,653

(22) Filed: Mar. 15, 2000

(51) Int. Cl.[7] ..... A01H 5/00
(52) U.S. Cl. ..... Plt./290
(58) Field of Search ..... Plt./287, 290, 296

(56) References Cited

U.S. PATENT DOCUMENTS 4,616,099 * 10/1986 Sparkes ..... 47/58

OTHER PUBLICATIONS

Shukla, et al., 1993, "Mutation studies on early and late varieties of garden chrysanthemums", J. Nuclear Agric. Biol., 22 (3–4):138–142.*
Broertjes, et al., 1980, "A mutant of a mutant of a . . . Irradiation of progressive radiation induced mutants in a mutation breeding programme with *Chrysanthemum morifolium*", Euphytica, 29:525–530.*
Gosling, ed., 1979, "The Chrysanthemum Manual—6$^{th}$ edition", The National Chrysanthemum Society, London, Essex Telegraph Press, Ltd., pp. 329–336.*
Broertjes, et al., 1978, "Application of Mutation Breeding Methods in the Improvement of Vegetatively Propagated Crops", Elsevier Sci Pub. Co., New York, pp 162–175.*
Searle, et al., 1968, "Chrystanthemums the Year Round", Blanford Press, London, pp. 27–29, 320–327.*
Chan, 1966, "Chrysanthemum and rose mutations induced by X–rays", Am. Soc. Hort. Sci. Proc., pp. 613–620.*
Broertjes, 1966, "Mutation breeding of chrysanthemums", Euphytica, 15:156–162.*
Dowrick, et al., 1966, "The induction of mutations in chrysanthemum using X– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Amber Pomona', characterized by its upright, outwardly spreading and uniformly mounded plant habit; freely branching, dense and full plants; dark green foliage; uniform flowering; nine-week flowering response time; large decorative-type inflorescences that are about 9.4 cm in diameter; light orange bronze-colored ray florets; and excellent postproduction longevity with inflorescences and leaves maintaining good substance and color for at least three weeks in an interior environment.

2 Drawing Sheets

BACKGROUND OF THE INVENTION

The present Invention relates to a new and distinct cultivar of Chrysanthemum plant, botanically known as *Dendranthema grandiflora* and hereinafter referred to by the cultivar name Amber Pomona.

The new Chrysanthemum is a product of a mutation induction breeding program conducted by the Inventor in Fort Myers, Fla. The objective of the program is to create new Chrysanthemum cultivars with desirable inflorescence form and floret colors, good substance, and excellent post-production longevity.

The new Chrysanthemum originated by exposing unrooted cuttings of the Chrysanthemum cultivar Orange Pomona, disclosed in U.S. Plant Pat. No. 11,176, to X-ray radiation in June, 1997, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Fort Myers, Fla. The new Chrysanthemum was discovered and selected by the Inventor as a single flowering plant within this population in January, 1998. The selection of this plant was based on its desirable inflorescence form and ray floret color.

Asexual reproduction of the new Chrysanthemum by terminal cuttings harvested in a controlled environment in Fort Myers, Fla., has shown that the unique features of this new Chrysanthemum are stable and reproduced true to type in successive generations.

SUMMARY OF THE INVENTION

The cultivar Amber Pomona has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Amber Pomona'. These characteristics in combination distinguish 'Amber Pomona' as a new and distinct Chrysanthemum:

1. Upright, outwardly spreading and uniformly mounded plant habit.
2. Freely branching, dense and full plants.
3. Dark green foliage.
4. Uniform flowering.
5. Nine-week flowering response time.
6. Large decorative-type inflorescences that are about 9.4 cm in diameter.
7. Light orange bronze-colored ray florets.

8. Excellent postproduction longevity with inflorescences and leaves maintaining good substance and color for at least three weeks in an interior environment.

Compared to plants of the parent cultivar, Orange Pomona, plants of the new Chrysanthemum have much lighter orange bronze-colored ray florets.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately descibe the actual colors of the new Chrysanthemum.

The photograph at the top of the first sheet comprises a side perspective view of a typical flowering plant of 'Amber Pomona'.

The photograph at the bottom of the first sheet comprises a close-up view of upper (left) and lower (right) surfaces of typical inflorescences and upper (left) and lower (right) surfaces of typical leaves of the cultivar Amber Pomona.

The photograph at the top of the second sheet comprises a side perspective view of typical flowering plants of 'Amber Pomona' (left) and 'Orange Pomona' (right).

The photograph at the bottom of the second sheet comprises a close-up view of typical inflorescences of plants of 'Amber Pomona' (left) and 'Orange Pomona' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the Autumn in Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbudded-types. Measurements and numerical values represent averages of typical flowering plants.

Botanical classification: *Dendranthema grandiflora* cultivar Amber Pomona.

Commercial classification: Decorative disbudded-type potted Chrysanthemum.

Parentage: Induced mutation of the *Dendranthema grandiflora* cultivar Orange Pomona, disclosed in U.S. Plant Pat. No. 11,176.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative potted Chrysanthemum typically grown as a disbudded-type. Inverted triangle; compact, stems upright and mostly outwardly spreading giving a uniformly mounded appearance to the plant. Freely branching; about three or four lateral branches develop after removal of terminal apex (pinching); dense and full plants.

*Plant height.*—Compact, about 25 cm.

*Plant width.*—About 46 cm.

*Stem description.*—Diameter: About 4 mm. Texture: Pubescent. Color: Close to 146B.

*Foliage description.*—Arrangement: Alternate. Length: About 7.3 cm. Width: About 5.4 cm. Apex: Cuspidate. Base: Cuneate to truncate. Margin: Palmately lobed, sinuses between lateral lobes mostly parallel. Texture: Upper and lower surfaces with very fine pubescence; veins prominent on lower surface. Petiole length: About 2.3 cm. Petiole diameter: About 3.5 mm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Decorative inflorescence form with elongated oblong-shaped ray florets. Inflorescences borne on terminals above foliage. Disk and ray florets arranged acropetally on a capitulum.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about nine weeks later.

*Postproduction longevity.*—Inflorescences and leaves will maintain good color and substance for at least three weeks in an interior environment.

*Quantity of inflorescences.*—As a disbudded-type, all lateral inflorescences are removed to allow for maximum terminal inflorescence size. One inflorescence per lateral stem; about three or four inflorescences per plant.

*Inflorescence bud.*—Height: About 7 mm. Diameter: About 9 mm. Color: Close to 143A.

*Inflorescence size.*—Diameter: About 9.4 cm. Depth (height): About 4.3 cm. Diameter of disc: About 5 mm, inconspicuous.

*Ray florets.*—Shape: Elongated, oblong. Orientation: Initially upright, incurved, then about 45° to perpendicular to peduncle. Length: About 4.8 cm. Width: About 9 mm. Apex: Acute, rounded or emarginate. Margin: Entire. Texture: Smooth, glabrous, satiny. Number of ray florets per inflorescence: Numerous, about 151. Color: When opening: Yellow, 12A, heavily overlaid with red, 46A to 46B to 42A. Fully opened, upper surface: 12A to 167A, faintly overlaid with red, 46A to 46B. Fully opened, lower surface: Close to 162A with very faint reddish, close to 46B, overtones.

*Disc florets.*—Shape: Tubular. Apex: Serrated. Length: About 7 mm. Width: Apex: About 1.5 mm. Base: About 1 mm. Number of disc florets per inflorescence: Few, about 28. Color: Immature: 154A. Mature: Apex: 7A. Mid-section: 154A. Base: White, 155D.

*Reproductive organs.*—Androecium: Present on disc florets only. Anther color: 9A. Pollen amount: Moderate to scarce. Pollen color: 17A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Amber Pomona', as illustrated and described.

* * * * *

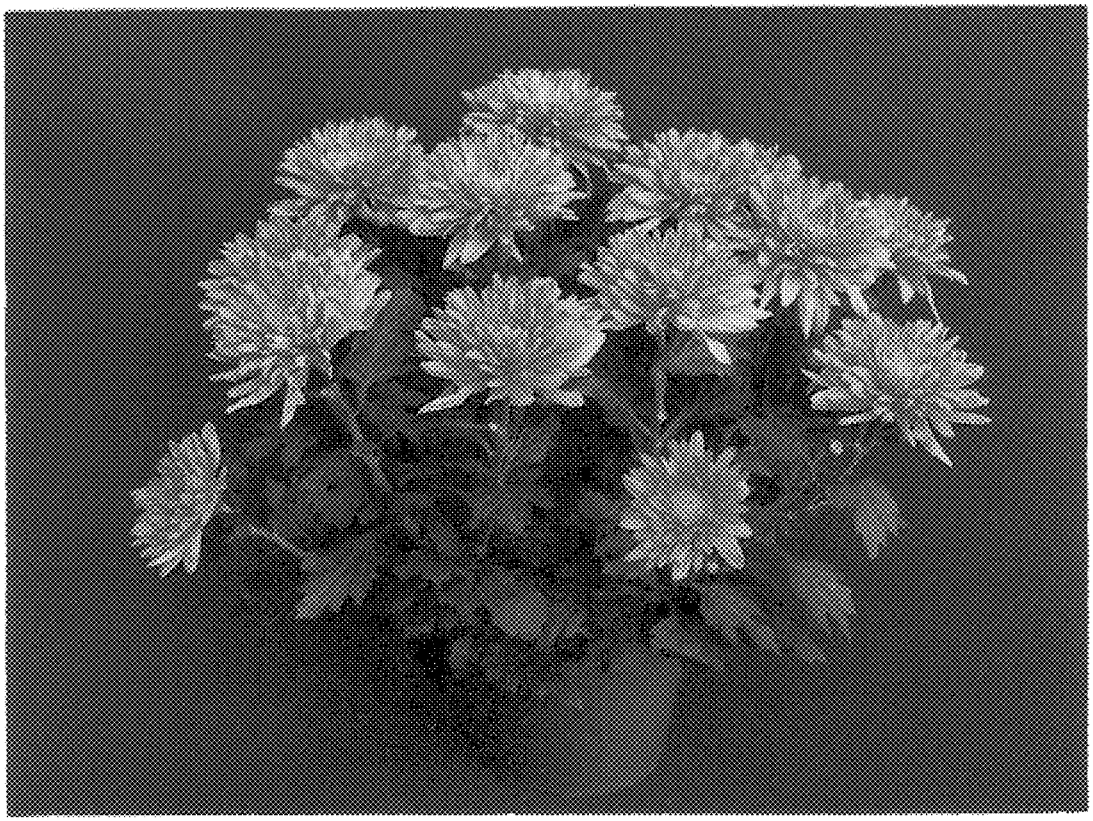
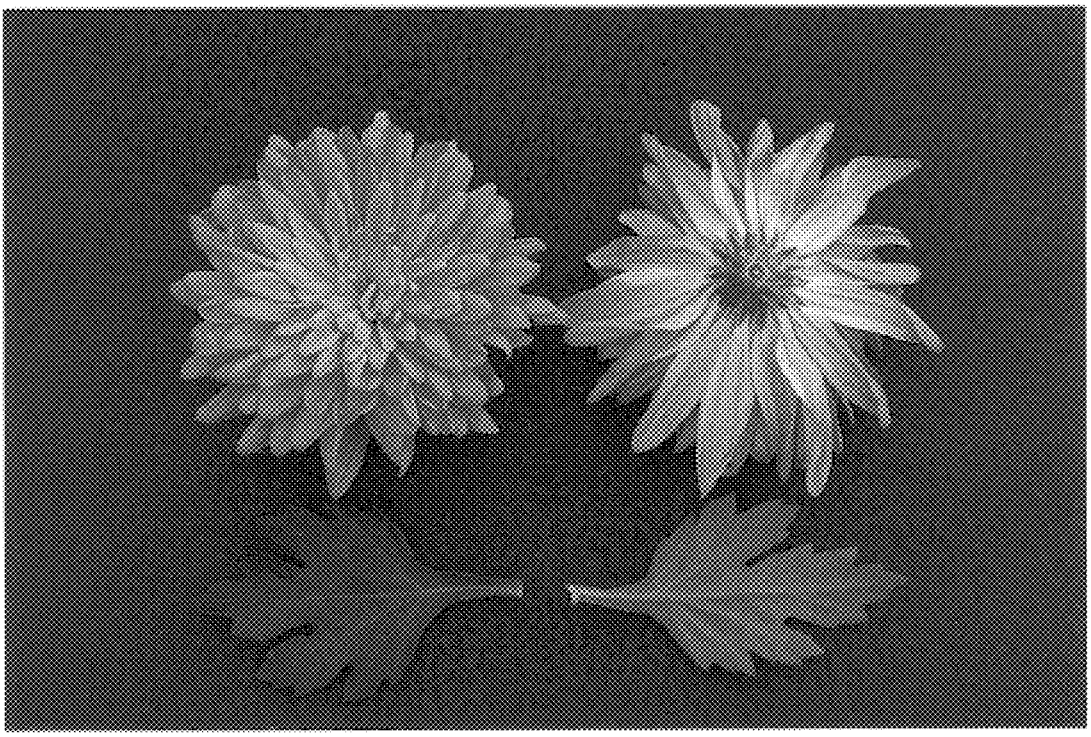

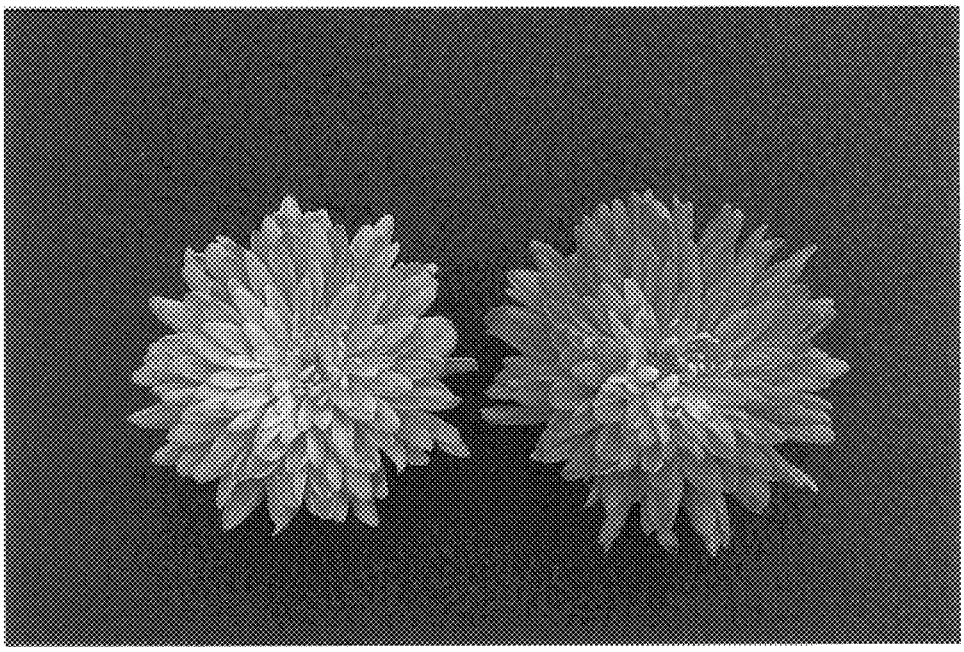

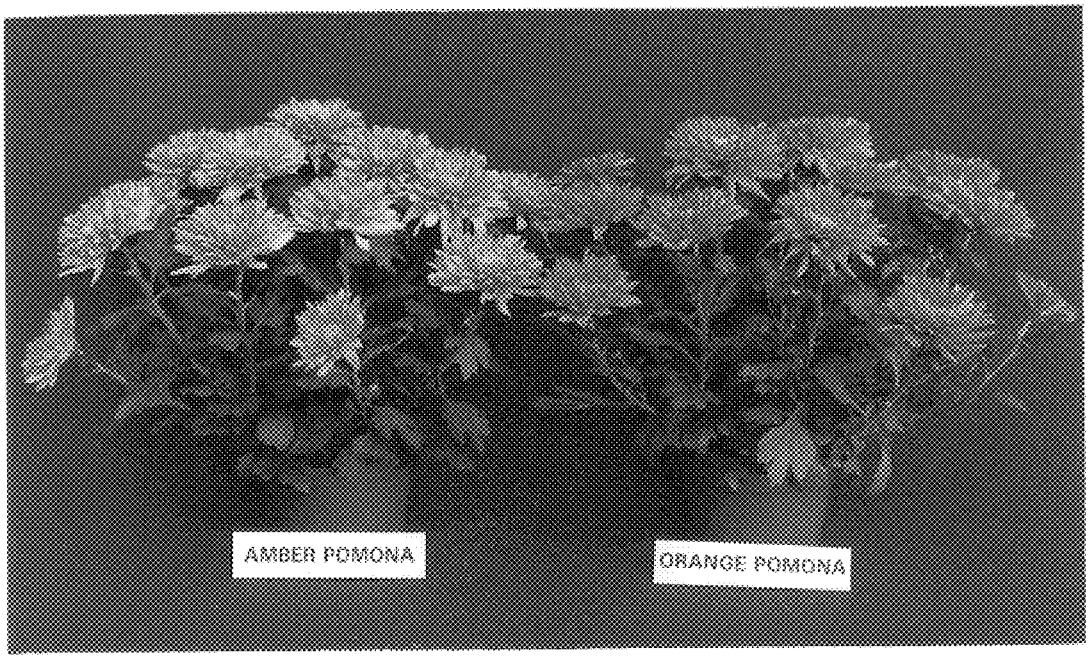
AMBER POMONA
ORANGE POMONA